(12) United States Patent
Iliopoulos et al.

(10) Patent No.: US 9,704,762 B2
(45) Date of Patent: Jul. 11, 2017

(54) APPLICATION OF IN-LINE GLASS EDGE-INSPECTION AND ALIGNMENT CHECK IN DISPLAY MANUFACTURING

(71) Applicant: Applied Materials, Inc., Santa Clara, CA (US)

(72) Inventors: Ilias Iliopoulos, Foster City, CA (US); Shuo Na, Sunnyvale, CA (US); Kelby Yancy, Forney, TX (US); Chunsheng Chen, Tianjin (CN)

(73) Assignee: APPLIED MATERIALS, INC., Santa Clara, CA (US)

( * ) Notice: Subject to any disclaimer, the term of this patent is extended or adjusted under 35 U.S.C. 154(b) by 45 days.

(21) Appl. No.: 14/610,441

(22) Filed: Jan. 30, 2015

(65) Prior Publication Data

US 2015/0221563 A1 Aug. 6, 2015

Related U.S. Application Data

(60) Provisional application No. 61/935,780, filed on Feb. 4, 2014.

(51) Int. Cl.
*H01L 21/00* (2006.01)
*H01L 21/66* (2006.01)
*H01L 21/67* (2006.01)
*C23C 16/52* (2006.01)
*G01N 21/95* (2006.01)
*C23C 14/52* (2006.01)
(Continued)

(52) U.S. Cl.
CPC ............. *H01L 22/12* (2013.01); *C23C 14/52* (2013.01); *C23C 14/56* (2013.01); *C23C 16/52* (2013.01); *C23C 16/54* (2013.01); *G01N 21/9503* (2013.01); *H01L 21/67201* (2013.01); *H01L 21/67259* (2013.01); *H01L 21/67288* (2013.01); *H01L 22/26* (2013.01)

(58) Field of Classification Search
CPC ......... H01L 21/67201; H01L 21/67288; H01L 21/681; H01L 21/67259; H01L 22/12; G06T 7/10; G06T 7/12; G06T 7/13; G01N 21/9503
USPC .................................... 438/7, 16; 356/237.5
See application file for complete search history.

(56) References Cited

U.S. PATENT DOCUMENTS

| 5,511,934 A * | 4/1996 | Bacchi ................... B65G 47/24 |
| | | 198/394 |
| 2008/0101912 A1* | 5/2008 | Martin ................ H01L 21/6719 |
| | | 700/254 |

(Continued)

*Primary Examiner* — Fernando L Toledo
*Assistant Examiner* — Aaron Gray
(74) *Attorney, Agent, or Firm* — Patterson + Sheridan, LLP

(57) ABSTRACT

Methods and apparatus for determining substrate integrity and alignment are described. Devices as described herein can include a transfer chamber, one or more process chambers, a loadlock chamber a first optical device, a second optical device and a radiation source positioned outside and above an opening for the loadlock chamber. Methods as described herein can include delivering a substrate to an opening in a process chamber, activating the optical device and the radiation source and capturing a plurality of images, extracting a substrate edge pattern from the plurality of images, comparing the substrate edge pattern to an expected edge pattern to determine a level of edge variance and adjusting or stopping a process if the level of edge variance is outside of an edge variation range.

5 Claims, 6 Drawing Sheets

(51) Int. Cl.
  *C23C 14/56* (2006.01)
  *C23C 16/54* (2006.01)

(56) References Cited

U.S. PATENT DOCUMENTS

| | | | | |
|---|---|---|---|---|
| 2011/0142572 A1* | 6/2011 | Blonigan | .......... | C23C 16/45565 414/217 |
| 2011/0199477 A1* | 8/2011 | Ravid | ............... | H01L 21/67253 348/87 |
| 2015/0287625 A1* | 10/2015 | Fujimoto | ............. | G01B 11/002 382/151 |

* cited by examiner

APPLICATION OF IN-LINE GLASS EDGE-INSPECTION AND ALIGNMENT CHECK IN DISPLAY MANUFACTURING

CROSS-REFERENCE TO RELATED APPLICATIONS

This application claims priority to U.S. Provisional Patent Application Ser. No. 61/935,780, filed on Feb. 4, 2014, which is incorporated by reference herein.

BACKGROUND

Field

Embodiments disclosed herein generally relate to an optical device for use with processed substrates and methods of use. More specifically, embodiments generally relate to substrate integrity and alignment in thin film deposition.

Description of the Related Art

Substrates must be scanned for defects both before any patterning is done and after patterning to identify sites with defects that would lead to a defective device. As substrates become larger and pattern features become smaller, the problem of scanning becomes more difficult. Methods or strategies for improved scanning for defects thus become increasingly important in keeping the cost of inspection in line with the cost of patterning the wafers in the first place. In addition, rapid scanning of wafers and similar devices is important for extended production runs to avoid an accumulation of defective substrates upon entrance to the chamber or defective processed substrates due to processing issues.

With shrinking pixel size and fast refresh rate, display manufacturers face novel challenges. These challenges require the manufacturers to better control defects, film properties and thickness as the glass thickness itself shrinks. The thickness of the glass itself is related to glass breakage, which is consistently a key issue at customer fabrication facilities. A glass breakage brings the tool to a costly unscheduled "down", or time period in which the tool is not active. A down due to glass breakage typically takes 18-24 hours to correct, making each down both expensive and non-productive. Further, aside from the lost productivity, the maintenance might require wet cleaning of the process chambers or transfer chambers to completely remove all microscopic debris which may remain in the chamber after the break.

Therefore, there is a need for improved devices and methods for substrate process control.

SUMMARY

Embodiments disclosed herein generally relate to substrate integrity and alignment in device manufacturing. In one embodiment, a processing device is provided. The processing device can include a transfer chamber, one or more process chambers, a loadlock chamber, a first optical device, a second optical device and a radiation source. The one or more process chambers can be in connection with the transfer chamber, the process chambers each including a processing entrance proximate the transfer chamber. The loadlock chamber can include a loadlock entrance and a loadlock exit, the loadlock entrance having an upper edge, a lower edge, a first lateral edge and a second lateral edge. The first optical device and a second optical device can be positioned outside of and above the upper edge of the loadlock entrance, where the first optical device is positioned to view the first lateral edge and the second optical device is positioned to view the second lateral edge. The radiation source can be positioned outside of and above the upper edge of the loadlock entrance, where the radiation source is positioned to deliver radiation at the first lateral edge and the second lateral edge.

In another embodiment, a method of measuring substrate attributes is provided. The method can begin by delivering a substrate to an opening in a process chamber, and the substrate having a deposition surface with lateral edges, the opening in the process chamber having at least two optical devices positioned to view the lateral edges of the substrate and a radiation source positioned outside of the opening to deliver radiation to the lateral edges of the substrate. The optical device can then be activated concurrent with the radiation source such that radiation is delivered to the lateral edges of the substrate at approximately the same time that the optical device captures a plurality of images. A substrate edge pattern can then be extracted from the plurality of images. The substrate edge pattern can then be compared to an expected edge pattern to determine a level of edge variance. If the level of edge variance is outside of an edge variation range, a process can be adjusted or stopped accordingly.

In another embodiment, a method of measuring substrate alignment is provided. The method can begin by positioning a substrate in a process chamber, the substrate having a first surface, a first lateral edge, a second lateral edge and a second surface opposite the first surface, the process chamber having an opening with at least two optical devices and a radiation source positioned outside and in connection therewith. One or more layers can then be deposited on the first surface of the substrate. The substrate can then be transferred out of the opening, where the transfer activates the optical devices and the radiation source. Radiation can then be emitted from the radiation source toward a plurality of points on the first surface, where the optical devices capture images in conjunction with the radiation emission. A substrate alignment pattern can then be extracted from the plurality of images, the substrate alignment pattern comprising substrate alignment as compared to the process chamber and layer alignment as compared to the first lateral edge and the second lateral edge. The substrate alignment pattern can then be compared to an expected alignment pattern to determine a level of substrate/chamber alignment variance and a level of layer/substrate alignment variance. Finally, if the level of substrate/chamber alignment variance or the level of layer/substrate alignment variance is outside of an alignment variation range, a process can then be adjusted or stopped.

BRIEF DESCRIPTION OF THE DRAWINGS

So that the manner in which the above recited features of the present invention can be understood in detail, a more particular description of the invention, briefly summarized above, may be had by reference to embodiments, some of which are illustrated in the appended drawings. It is to be noted, however, that the appended drawings illustrate only typical embodiments of this invention and are therefore not to be considered limiting of its scope, for the invention may admit to other equally effective embodiments.

To facilitate understanding, identical reference numerals have been used, where possible, to designate identical elements that are common to the figures. It is contemplated that elements disclosed in one embodiment may be beneficially utilized on other embodiments without specific recitation.

DETAILED DESCRIPTION

Figure 1A:
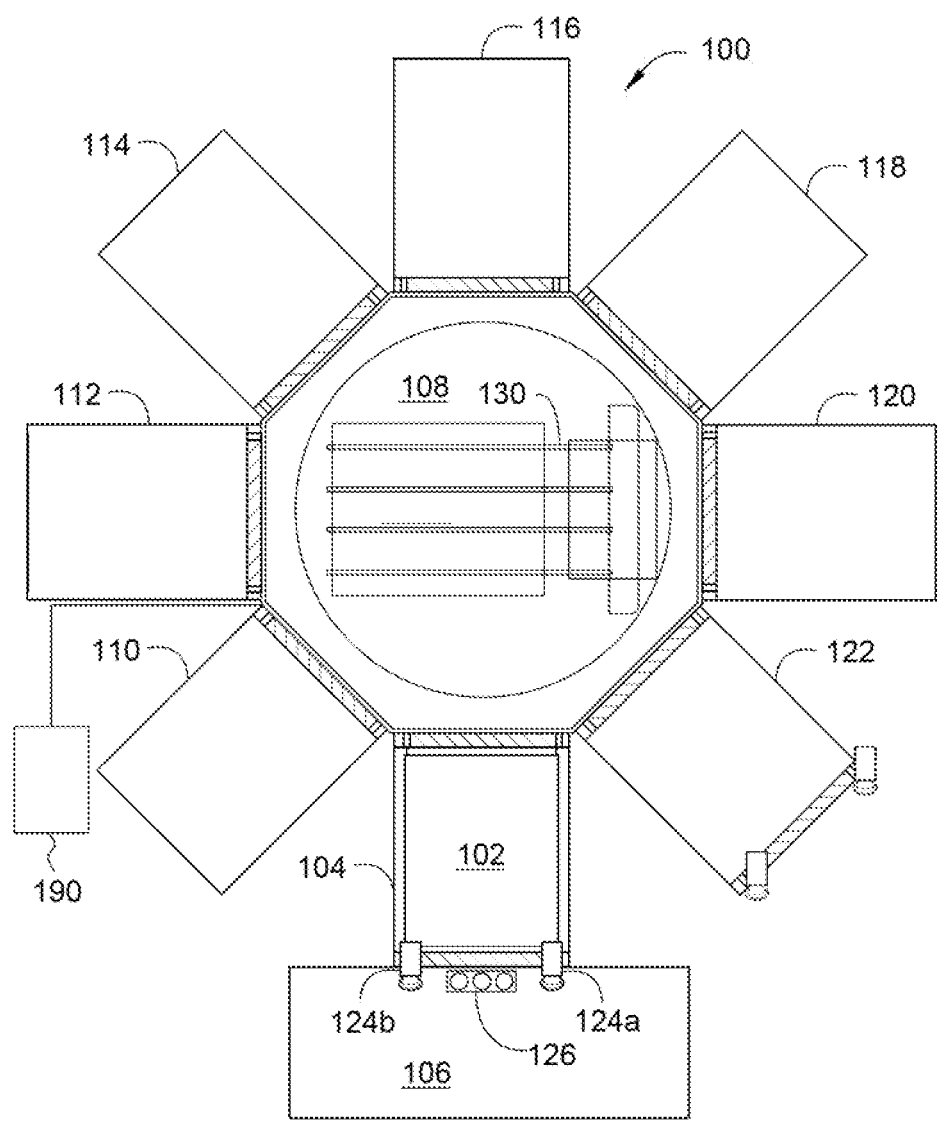
FIG. 1A shows a top plan view of an substrate processing system suitable for depositing silicon-containing layers on a substrate, according to one embodiment.

Embodiments disclosed herein generally relate apparatus and methods for monitoring and controlling a large area substrate processing system. The concept of the invention can be applied to substrates greater than 750 cm$^2$, such as substrates greater than 2000 cm$^2$, substrates greater than 15000 cm$^2$, or substrates greater than 40000 cm$^2$. The present methods and devices provide solutions for substrate integrity and alignment in device manufacture, such as in display manufacturing.

The solution is based on measuring the intensity of direct light reflection from the glass substrate. This is challenging in the display tool because of the high speed at which the glass is moving, loading robot interference, and the need for inspection accuracy. Detecting cracks and misalignments is complicated by the fast substrate motion, which typically moves at speeds of 0.2 meters per second to 2.0 meters per second, and by complex metal patterns on the substrate. As such, the embodiments here employ high speed image capturing capabilities and the use of a high speed processing controller in order to prevent false alarms.

In one embodiment, defect inspection on glass substrates is done using bright field light, with the light above the substrate. As such, both the cameras and the LED lights are placed above the substrate plane. The image is taken simultaneously with each light strobe. The substrate can be inspected for imperfections and defects as it enters the loadlock, as it exits the loadlock or as it enters/exits other accompanying chambers. After processing and as the substrate exits the loadlock the deposited, substrate can be checked again. At this point, the substrate can be checked for alignment of the substrate itself, for alignment of the deposited layers against the substrate edges and for any additional cracks which may have formed or been otherwise created during processing. The cameras must be able to cover both focal areas without loss in resolution Deposited layers can include but are not limited to amorphous silicon (a-Si), silicon nitride (SiNx) and silicon oxide (SiOx) layers, which are part of a group referred to generically as silicon-containing layers. These layers can be deposited using Applied Materials AKT deposition tools. The developed in-line edge inspection and alignment tools and methods have limited impact on throughput and robot movement.

The deposited layers can be processed in high volume and high throughput by different types of process chambers, for example, physical vapor deposition (PVD) and sputtering chambers, ion metal implant (IMP) chambers, chemical vapor deposition (CVD) chambers, atomic layer deposition (ALD) chambers, plasma etching chambers, annealing chambers, other furnace chambers, cleaning stations, etc. The substrate processing system may include a deposition chamber in which a substrate is exposed to one or more gas-phase materials or plasma. In one embodiment, the substrate processing system is also configured to include various types of process chambers to perform different etching, deposition, annealing, and cleaning processes.

For systems with PVD and/or CVD process chambers, the performance or condition of the PVD and/or CVD process chambers can be monitored and controlled by using metrology tools to collect post-processing film information, such as film thickness, film composition, film uniformity, and the like, after substrate processing. The measurement information can be used to detect a fault in the system, which may cause the measured data to suddenly fall outside a predetermined control range or the measured data trend differs from the normal data trend. Once the fault is detected, the system can be set up to prevent further substrate processing until the source(s) of fault is identified or corrected. The embodiments disclosed herein are more clearly described with reference to the figures below.

The measurement can be performed in-situ, which occurs in the process chamber, or ex-situ, which occurs outside the process chamber. In one embodiment, a cluster type substrate processing system 100, as shown in FIG. 1A, including a plurality of process chambers, for example chambers 110, 112, 114, 116, 118 and 120. At least one of which is a chemical vapor deposition (CVD) chamber, for example chamber 110. In another embodiment, the substrate processing system is also configured to include other types of process chambers, for example chambers 112, 114, 116, 118 and 120, configured to perform additional etching, deposition, annealing, and cleaning processes.

FIG. 1A shows a top plan view of an exemplary substrate processing system 100 suitable for depositing silicon-containing layers on a substrate 102. The substrate processing system 100 can include a transfer chamber 108 coupled to a factory interface 106 via a loadlock chamber 104. The factory interface 106 generally includes one or more substrates stored therein or substrate storage cassettes. The substrate storage cassettes are typically removably disposed in a plurality of storage bays/compartments formed inside the factory interface 106. The factory interface 106 may also include an atmospheric robot, such as a dual blade atmospheric robot. The atmospheric robot is adapted to transfer one or more substrates between the one or more substrate storage cassettes and the loadlock chamber 104. Typically, the factory interface 106 is maintained at or slightly above atmospheric pressure and the loadlock chamber 104 is disposed to facilitate substrate transfer between a vacuum environment of the transfer chamber 108 and a generally ambient environment of the factory interface 106. The substrate 102 processed by the substrate processing systems can be transferred from the factory interface 106 to the loadlock chamber 104 for processing of a fabrication sequence including two or more metal layer depositions on one or more substrates 102 without the substrate 102 leaving the system 100. Transfer robot 130 can transfer substrates between transfer chamber 108, process chambers 110, 112, 114, 116, 118 and 120, and a loadlock chamber 122. The process chambers 110, 112, 114, 116, 118 and 120 can be a PECVD chamber available from AKT America, Inc., a subsidiary of Applied Materials, Inc., located in Santa Clara, Calif. It is to be understood that the invention has applicability in other chambers as well, including apparatus available from other manufacturers.

Shown here, an optical devices 124a and 124b are positioned at the entrance of the loadlock chamber 122. The optical devices 124a and 124b is depicted as having one or more radiation sources 126. The number of light sources in the one or more radiation sources 126, shown here as three, is limited only by the available space to position the one or more radiation sources 126 on the optical devices 124a and 124b. In one embodiment, the one or more radiation sources 126 includes ten (10) radiation sources. The optical devices 124a and 124b are positioned such that the one or more radiation sources 126 are facing the upper surface of the substrate 102.

The optical devices 124a and 124b use high speed video capture to measure the edges of the substrate as the substrate passes in proximity to the captured region. The optical devices 124a and 124b may be, for example, be a camera capable of capturing images at 2 megapixels or greater. The camera can be configured to receive images at a constant interval while the one or more radiation sources 126 strobe radiation at a substantially similar frequency. The wavelength used and other radiation parameters can be used to provide optimal contrast between the substrate and deposited layers. In one example, the one or more radiation sources produce a broad spectrum white light.

The measurement can be done upon entrance to or exit from one or more of the transfer chamber 108, the loadlock chamber 104, the process chambers, 110, 112, 114, 116, 118 and 120, or loadlock chamber 122. For systems for processing large area substrates, the transfer chamber 108, the loadlock chamber 104, the process chambers, 110, 112, 114, 116, 118 and 120, and loadlock chamber 122 are all sized to accommodate large area substrates. Each of the transfer chamber 108, the loadlock chamber 104, the process chambers, 110, 112, 114, 116, 118 and 120, and separate loadlock chamber 122 can include multiple loadlock tools to collect pre-processing and post-processing data on the substrates.

For process control purposes, a user can measure substrate attributes, such as visibly cracked or stressed regions, film positioning and substrate positioning, both before and after deposition in the process chamber. If the measured data fall out of the control range, the system can receive a control signal to either remove a single substrate from further processing or to suspend further substrate processing until the cause of process drift is identified. For example, the substrate 102 is passed from the factory interface 106 through the entrance to the loadlock chamber 104. At the entrance to the loadlock chamber 104, the substrate 102 is measured for integrity and positioning by the optical devices 124a and 124b in conjunction with the radiation sources 126. Based on these measurement, the substrate 102 is spatial orientation and usability of the substrate 102 is determined.

Once the substrate 102 is determined to be useable and properly oriented, the substrate 102 can be placed in a CVD chamber 110 to deposit a first layer, such as a silicon-containing layer. After the layer deposition, the post-deposition layer properties of the substrate 102 can again be measured by optical devices located at the entrance/exit of the process chamber 110, the transfer chamber 108, a loadlock chamber 122, or loadlock chamber 104. In one embodiment, after a silicon-containing layer is deposited on the substrate 102, the substrate 102 is delivered through the loadlock chamber 122 to measure post-deposition properties, such as layer positioning. After the post-deposition properties have been measured, the substrate 102 can be placed in another chamber 112 to deposit a second layer.

After the second layer deposition, the post-deposition properties of the second layer on the substrate 102 can be measured by further optical devices placed at the entrance/exit of process chamber 112, the transfer chamber 108, a loadlock chamber 122, or loadlock chamber 104. The measurement can be performed on each of the layers, such as for control of both chambers. The measurement can be performed on only one layer, such as to monitor and control only one chamber. When more than one process chamber is used, it is possible that only one chamber is selected to be monitored and controlled. The substrate processing system 100 is controlled by a system control unit 190, which could include controller(s), computer(s), and memory (or memories).

Figure 1B:
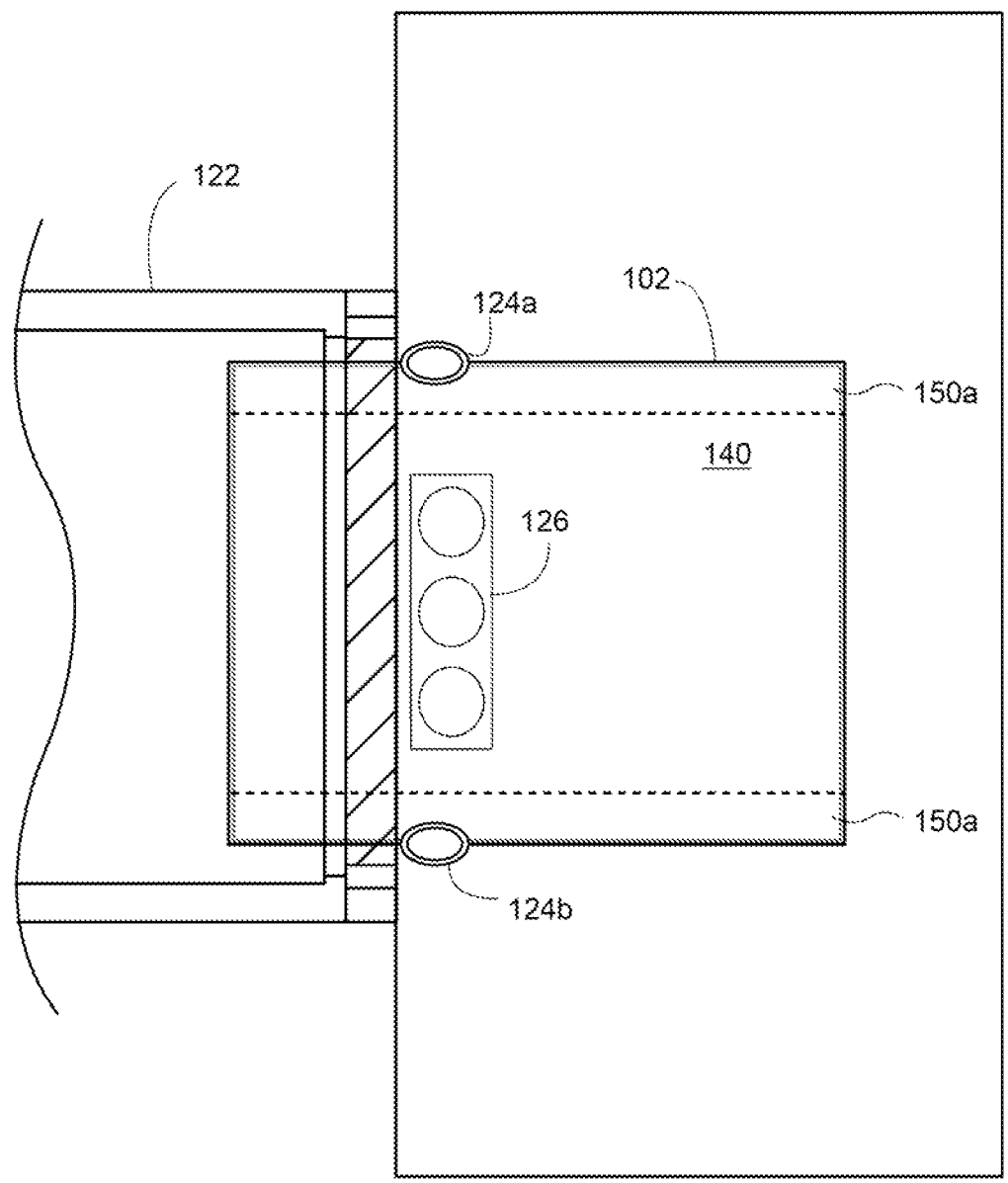
FIG. 1B depicts the substrate measured using optical devices according to one embodiment.

FIG. 1B depicts the substrate 102 measured according to one embodiment. The substrate 102 can have one or more deposited layers 140. The deposited layers 140 can be composed of amorphous silicon (a-Si), polycrystalline silicon, silicon nitride (SiNx), silicon oxide (SiOx) or combinations thereof. The substrate 102 is then delivered through the loadlock chamber 122 and over the optical devices 124a and 124b.

Each of the optical devices 124a and 124b measures one or more of the substrate attributes of the substrate 102 and/or the deposited film 140 in the regions which are visible to the optical device, shown here as the edges of the substrate 102. Though the regions 150a and 150b are depicted as the edges, the regions 150a and 150b may overlap or not meet. In some embodiments, the regions 150a and 150b will not completely cover the surface area of the substrate 102. Thus, the optical devices 124a and 124b here would measure only the edges of the substrate 102 and the deposited layer 140.

In this embodiment, the measurements of the substrate attributes are taken during standard movement of the substrate 102 from the loadlock chamber 122. In one embodiment, the substrate 102 is moving at a speed of from 0.2 meters per second to 2.0 meters per second. As the substrate 102 passes over the optical devices 124a and 124b, the optical devices 124a and 124b are alerted to the presence of the substrate 102 by a signal, such as a signal received from a substrate presence detector (not shown). In response to the signal received, the radiation source 126 delivers radiation to the substrate 102. Information on the substrate attributes of the substrate 102 at the regions 150a and 150b is visually recorded by the optical device 124a and 124b. The radiation produced by the radiation source 126 increases the contrast between the substrate 102 the deposited layer 140 and the background environment, which allows for better visualization of cracks, abrasions and other defects which may affect further processing.

Though shown herein in conjunction with the loadlock chamber 122, the measurement of substrate attributes may be done during any movement of substrate 102 between chambers. In one example, the substrate 102 is measured upon exiting or entering one of the process chambers 110, 112, 114, 116, 118 and 120.

Figure 1C:
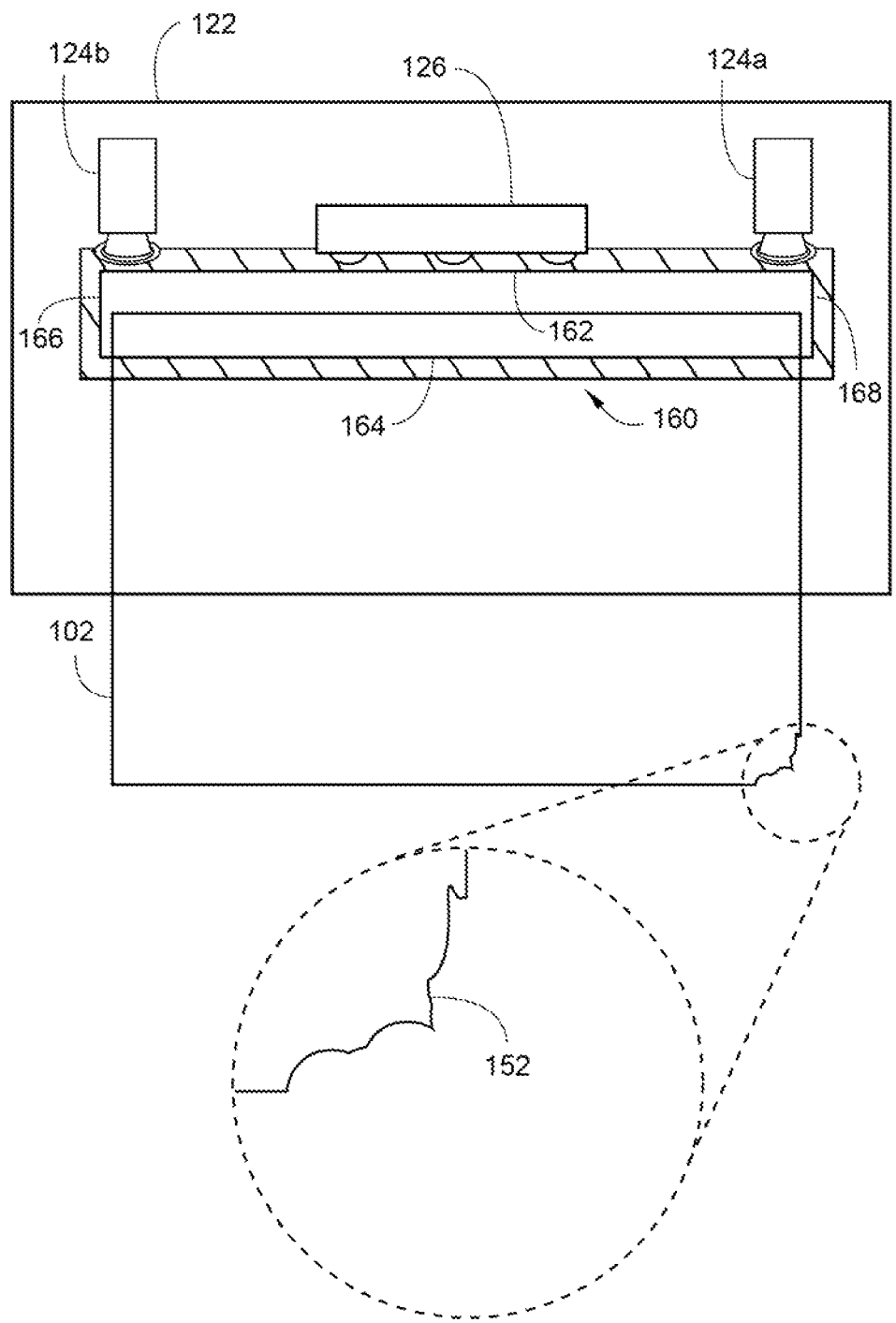
FIG. 1C depicts a front view of the loadlock chamber, according to one embodiment.

FIG. 1C depicts a front view of the loadlock chamber 122, according to one embodiment. The loadlock chamber 122 includes an opening 160 with the optical devices 124a and 124b and the radiation source 126. The opening includes an upper wall 162, a lower wall 164, a first sidewall 166 and a second sidewall 168. The substrate 102 is delivered to the opening 160 where images of the edges of substrate 102 are captured. The images are processed to detect damage and orientation of the substrate 102 upon entry into the loadlock chamber 122.

The optical devices 124a and 124b and the radiation source 126 are positioned above upper wall 162 of the opening 160, so as to limit any effect of the position of the optical devices 124a and 124b. The radiation is delivered to the substrate 102 in a strobing manner (i.e. intermittent and rhythmic on and off) such that the light is flashed during the image capture.

As shown here, the substrate 102 moves through the opening 160, the optical device 124a detects a damaged edge 152 of the substrate 102. Upon detecting the damaged edge 152, the movement of the substrate 102 can be stopped. The substrate 102 can be stopped based on any detectable damage or based on damage which crosses a variance threshold. The variance threshold is the amount of variance which is tolerable without the substrate breaking or otherwise being unusable. In one embodiment, the variance threshold is a single crack or chip.

Figure 2:
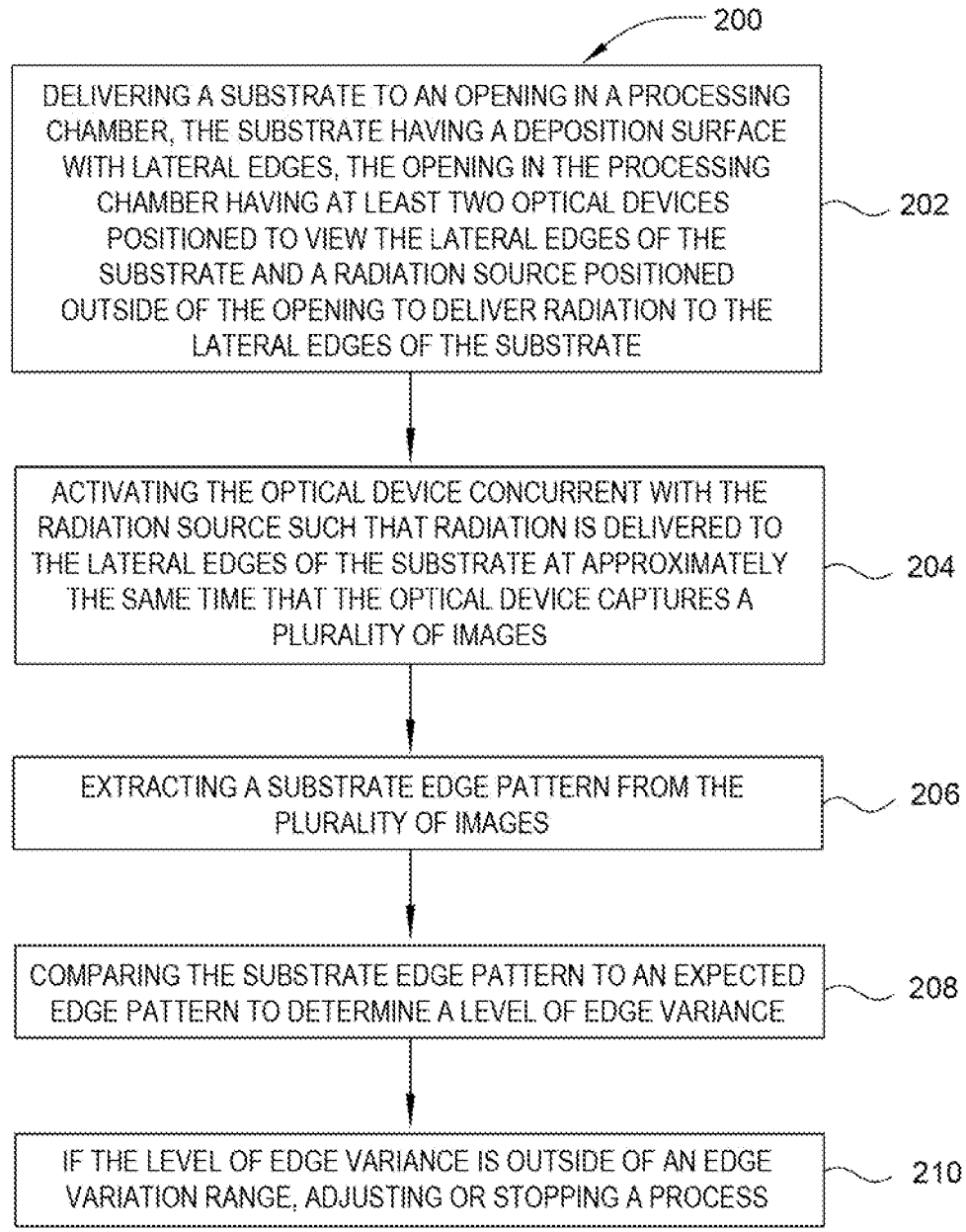
FIG. 2 is a block diagram of a method for monitoring substrate integrity, according to one embodiment.

FIG. 2 is a block diagram of a method 200 for monitoring substrate integrity, according to one embodiment. The method 200 includes delivering a substrate to an opening in a process chamber, the substrate having a deposition surface with lateral edges, the opening in the process chamber having at least two optical devices positioned to view the lateral edges of the substrate and a radiation source positioned outside of the opening to deliver radiation to the lateral edges of the substrate, at block 202; activating the optical device concurrent with the radiation source such that radiation is delivered to the lateral edges of the substrate at approximately the same time that the optical device captures a plurality of images, at block 204; extracting a substrate edge pattern from the plurality of images, at block 206; comparing the substrate edge pattern to an expected edge pattern to determine a level of edge variance, at block 208; and if the level of edge variance is outside of an edge variation range, adjusting or stopping a process, at block 210.

The method 200 begins by delivering a substrate to an opening in a process chamber, at block 202. The substrate has a deposition surface which, as shown in FIGS. 1A-1C, faces upward. The substrate further has lateral edges which form the width boundary of the substrate. The substrate can be a standard substrate used in the production of semiconductor devices, such as in the production of displays. The substrate may be, among others, a thin sheet of metal, plastic, organic material, silicon, glass, quartz, or polymer materials. In one embodiment, the substrate is a glass substrate upon which a silicon-containing layer will be deposited. In other embodiments, the substrate may be doped or otherwise modified glass substrate. The substrate may have a surface area greater than about 1 square meter, such as greater than about 2 square meters. Further, the substrate may be a large-sized substrate having a plan surface area of about 15,600 cm$^2$, or greater, for example about a 90,000 cm$^2$ plan surface area.

The opening in the process chamber can have at least two optical devices. The optical devices are positioned to view the lateral edges of the substrate. At least one radiation source is positioned outside of the opening and in conjunction with the optical devices. In one embodiment, the radiation source is positioned between the optical devices. In another embodiment, each optical device uses a separate radiation source. The radiation sources are configured to deliver radiation to at least the lateral edges of the substrate.

Once the substrate is at the opening of the process chamber, the optical devices are then activated concurrent with the radiation source, at block 204. The optical devices can be activated to deliver radiation by a number of means. In one embodiment, the optical device uses a time based approach to determine when the substrate will be positioned under the optical device. In another embodiment, the optical monitoring system is activated by a substrate detector. The substrate detector may be a device for detecting motion in proximity to the optical device or in proximity to the entrance/exit, which can include a motion sensor.

The radiation from the radiation source is delivered to the lateral edges of the substrate at approximately the same time that the optical device captures a plurality of images. It is believed that by strobing the radiation to the surface of the substrate during the capture process, the contrast between the damaged areas and undamaged surrounding areas can be better visualized. The radiation sources deliver radiation of both a frequency and interval to increase the contrast of cracks and abrasions on the substrate as compared to the undamaged portions of the substrate.

Using the images collected from the optical device, a substrate edge pattern is extracted, at block 206. The substrate edge pattern is the deviations of the edge from an undamaged edge. The images collected at various points of contrast are accumulated and processed to create the substrate edge pattern.

The substrate edge pattern is then compared to an expected edge pattern to determine a level of edge variance, at block 208. The expected edge pattern can be either empirically derived or defined based on an imaginary perfectly straight edge. The deviations from the undamaged edge can be deleterious, cumulatively deleterious or innocuous. Deleterious deviations create a high likelihood that the substrate will break or otherwise fail during processing. Cumulatively deleterious deviations are deviations that if too many of them occur or if they cover a certain proportion of the substrate, create a high likelihood that the substrate will break or otherwise fail during processing. Innocuous deviations are deviations which are neither deleterious nor cumulatively deleterious. Innocuous deviations can include deviations which will not affect device performance or substrate integrity during processing.

The level of edge variance is the edge difference as compared to the expected edge pattern. The level of edge variance can be expressed as a percentile change or as a quantity and intensity of the deviation or combinations thereof.

Finally, if the level of edge variance is outside of an edge variation range, a process can be adjusted or stopped, at block 210. The process can be any action performed by the chamber, either autonomously or with user interaction. In the case of deleterious deviations, the substrate may be removed from processing if found (i.e. single instance creates a level of edge variance outside of the acceptable edge variation range). In the case of cumulatively deleterious deviations, the substrate may be removed from processing if the number or percentile amount found crosses a deviation threshold (i.e. multiple instance creates a level of edge variance outside of the acceptable edge variation range). Therefore, innocuous variances or cumulatively deleterious variances which are below the threshold do not affect substrate processing.

Figure 3A:
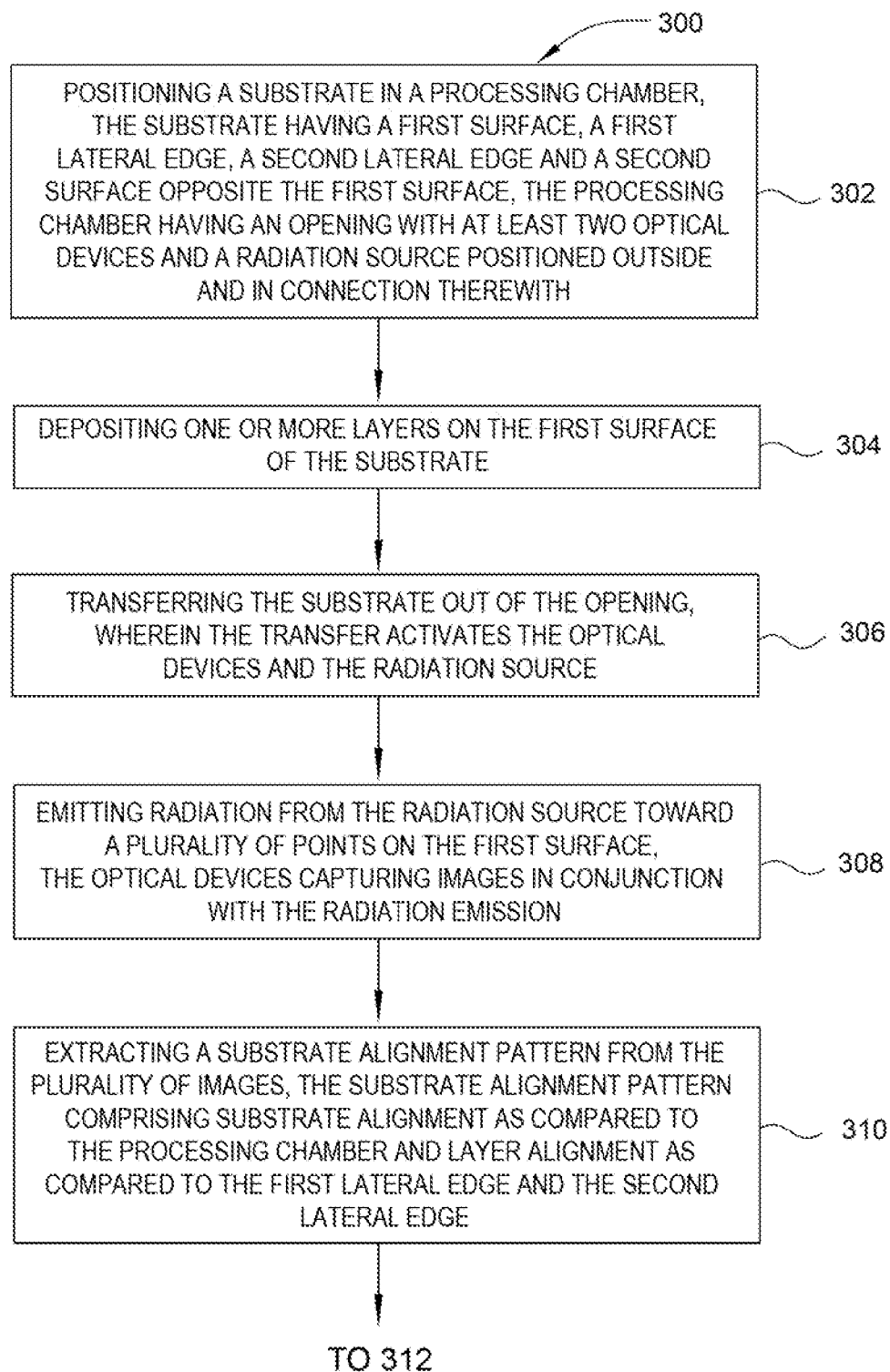
FIGS. 3A and 3B are a block diagram of a method for monitoring substrate and layer alignment, according to one embodiment.
Figure 3B:
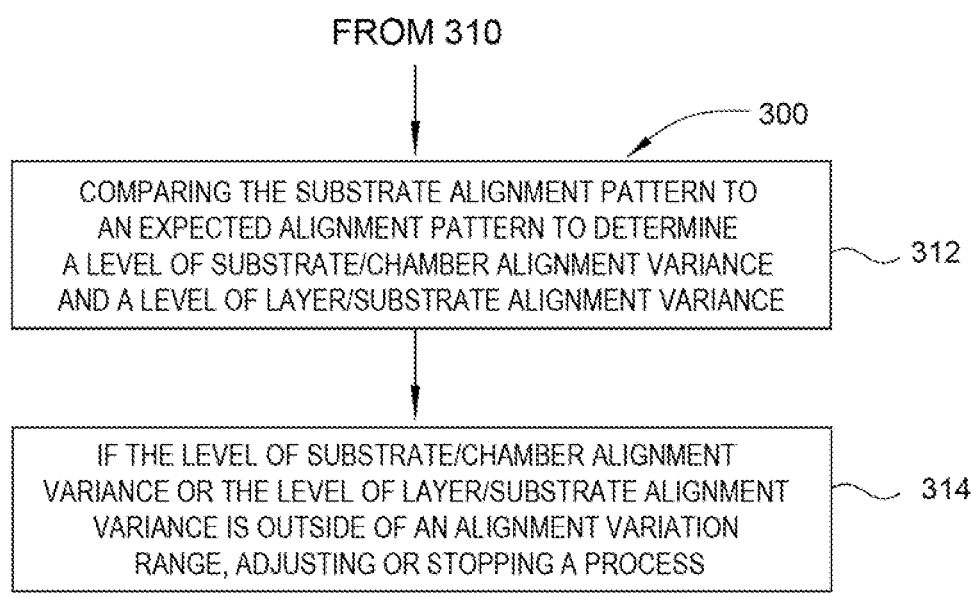

FIGS. 3A and 3B are a block diagram of a method 300 for monitoring substrate and layer alignment, according to one embodiment. The method 300 includes positioning a substrate in a process chamber, the substrate having a first surface, a first lateral edge, a second lateral edge and a second surface opposite the first surface, the process chamber having an opening with at least two optical devices and a radiation source positioned outside and in connection therewith, at block 302; depositing one or more layers on the first surface of the substrate, at block 304; transferring the substrate out of the opening, wherein the transfer activates the optical devices and the radiation source, at block 306;

emitting radiation from the radiation source toward a plurality of points on the first surface, the optical devices capturing images in conjunction with the radiation emission, at block 308; extracting a substrate alignment pattern from the plurality of images, the substrate alignment pattern comprising substrate alignment as compared to the process chamber and layer alignment as compared to the first lateral edge and the second lateral edge, at block 310; comparing the substrate alignment pattern to an expected alignment pattern to determine a level of substrate/chamber alignment variance and a level of layer/substrate alignment variance, at block 312; and if the level of substrate/chamber alignment variance or the level of layer/substrate alignment variance is outside of an alignment variation range, adjusting or stopping a process, at block 314.

The method 300 begins with positioning a substrate in a process chamber, at block 302. The substrate has a first surface, a first lateral edge, a second lateral edge and a second surface opposite the first surface. The process chamber having an opening with at least two optical devices and a radiation source positioned outside and in connection therewith. The substrate used here can be the same as the substrate described with reference to FIG. 2. The optical devices and the radiation source can be as described with reference to FIGS. 1A-1C.

One or more layers can then be deposited on the first surface of the substrate, at block 304. The deposited layer can include a variety of materials, including but not limited to dielectric materials (e.g., $SiO_x$, $SiO_xN_y$, derivatives thereof or combinations thereof), semiconductive materials (e.g., Si and dopants thereof), barrier materials (e.g., $SiN_x$, $SiO_xN_y$ or derivatives thereof), or amorphous silicon or microcrystalline silicon thin film transistor (TFT) passivated by silicon-containing dielectric layer. Specific examples of dielectric materials and semiconductive materials that are formed or deposited by the process chamber onto the substrates may include, but is not limited to epitaxial silicon, polycrystalline silicon, amorphous silicon, microcrystalline silicon, silicon germanium, silicon dioxide, silicon oxynitride, silicon nitride, dopants thereof (e.g., B, P, or As), derivatives thereof or combinations thereof.

The substrate can then be transferred out of the opening, at block 306. Once the layer is deposited on the substrate, the substrate can then be moved to another chamber or out of the processing system. The movement of the substrate is generally facilitated by a transfer robot, as described with reference to FIG. 1A. The movement of the substrate can be related to the activation of the optical devices and the radiation source. The radiation source, the optical devices or combinations thereof can be activated using motion sensing devices, timers, or other devices which correlate the movement of the substrate and the activation of the radiation source and/or the optical devices.

Once activated, radiation can be emitted from the radiation source toward a plurality of points on the first surface, at block 308. The radiation can be delivered to a specific point on the surface or across the width of the surface such that at least the edge of the substrate, the edge of the layer or combinations thereof are captured in the plurality of images. The optical devices can capture the plurality of images in conjunction with the radiation emission, as described with reference to FIGS. 1B, 1C and 2. The plurality of images are then stored or transferred for further processing.

A substrate alignment pattern is then extracted from the plurality of images, at block 310. The substrate alignment pattern includes the substrate alignment or position as compared to the process chamber. The substrate alignment pattern can include position, orientation and movement of the substrate as determined from the plurality of images based on a stationary point or points, such as a portion of the chamber. The layer alignment can be determined based on the first lateral edge and the second lateral edge of the substrate.

The substrate alignment pattern can then be compared to an expected alignment pattern to determine a level of substrate/chamber alignment variance and a level of layer/substrate alignment variance, at block 312. The substrate/chamber alignment variance includes position, orientation and direction of motion for the substrate as compared to the expected alignment pattern of the substrate as compared to the chamber for each parameter. The expected alignment pattern includes position, orientation and direction of motion values which can be determined empirically or established based on desired position, orientation, and direction of motion for the substrate. The layer/substrate alignment variance includes position and orientation of the layer as compared to the expected alignment pattern of the layer as compared to the substrate for each parameter. The expected alignment pattern includes position and orientation values which can be determined empirically or established based on desired position and orientation for the layer.

Finally, if the level of substrate/chamber alignment variance or the level of layer/substrate alignment variance is outside of an alignment variation range, a process can be adjusted or stopped, at block 314. The alignment variation range is a range of acceptable shift of either the substrate as compared to the chamber or the layer as compared to the substrate. The alignment variation range can be a percentile which represents all position, orientation and direction of motion changes. In another embodiment, the alignment variation range can be individual percentile changes at each of the position, orientation and the direction of motion. In another embodiment, the alignment variation range can include position on each of the X, Y and Z axis of the coordinate plane, specific variation in orientation at the pitch, yaw and roll and direction of motion establishing variance from an expected travel path.

If variation beyond an acceptable range occurs, the process can be either stopped or adjusted depending on available options and the level of change necessary to reposition. The process can be any action performed by the chamber, either autonomously or with user interaction. The adjustment can prevent damage from occurring to the substrate and prevent improperly deposited layers from undergoing further processing.

The embodiments of the invention described herein generally relate to the integrity and alignment detection for a substrate. An optical device and a radiation source are positioned above the entrance or exit of a chamber. As the substrate crosses the threshold of the entrance or exit of the chamber, the optical device and the radiation source are activated to direct strobed radiation toward the substrate. The substrate receives the strobed radiation during the image capture process creating a high contrast plurality of images. The position, orientation, direction of motion and the integrity of the substrate are compared to expected values to determine if a subsequent process should be performed or if the substrate should be adjusted or discarded.

While the foregoing is directed to embodiments of the present invention, other and further embodiments of the invention may be devised without departing from the basic scope thereof, and the scope thereof is determined by the claims that follow.

The invention claimed is:

1. A processing device comprising:
   a transfer chamber;
   one or more process chambers in connection with the transfer chamber, the process chambers each comprising a processing entrance proximate the transfer chamber;
   a loadlock chamber comprising a loadlock entrance and a loadlock exit, the loadlock entrance having an upper wall, a lower wall, a first sidewall and a second sidewall;
   a first optical device and a second optical device positioned in a factory interface outside of and above the upper wall of the loadlock entrance, the first optical device positioned to view a first lateral edge of a substrate and the second optical device positioned to view a second lateral edge of the substrate; and
   a radiation source positioned in the factory interface between the first optical device and the second optical device and outside of and above the upper wall of the loadlock entrance, the radiation source positioned to deliver radiation at the first lateral edge and the second lateral edge.

2. The processing device of claim 1, wherein the first optical device and the second optical device comprise a camera.

3. The processing device of claim 1, wherein a first optical axis of the first optical device and a second optical axis of the second optical device are positioned perpendicular to the upper wall.

4. The processing device of claim 1, further comprising a plurality of first optical devices and a plurality of second optical devices.

5. The processing device of claim 1, wherein at least one of the process chambers is a CVD process chamber.

* * * * *